United States Patent
Chen et al.

(10) Patent No.: US 10,405,831 B2
(45) Date of Patent: Sep. 10, 2019

(54) MEDICAL IMAGE PLAYING SYSTEM AND METHOD

(71) Applicant: TAIHAO MEDICAL INC., Taipei (TW)

(72) Inventors: Rong-Tai Chen, Taichung (TW); Ruey-Feng Chang, Taichung (TW); Jie-Fan Chang, Taichung (TW); Heng Chen, Taipei (TW); Chung-Ming Lo, New Taipei (TW); Hsin-Hung Lai, Taipei (TW)

(73) Assignee: TAIHAO MEDICAL INC., Taipei (TW)

( * ) Notice: Subject to any disclaimer, the term of this patent is extended or adjusted under 35 U.S.C. 154(b) by 852 days.

(21) Appl. No.: 15/007,233

(22) Filed: Jan. 27, 2016

(65) Prior Publication Data
US 2016/0232945 A1    Aug. 11, 2016

(30) Foreign Application Priority Data

Feb. 10, 2015  (TW) .............................. 104104365 A

(51) Int. Cl.
G11B 27/36  (2006.01)
A61B 8/00  (2006.01)

(52) U.S. Cl.
CPC .............. *A61B 8/463* (2013.01); *A61B 8/465* (2013.01); *A61B 8/469* (2013.01)

(58) Field of Classification Search
None
See application file for complete search history.

(56) References Cited

U.S. PATENT DOCUMENTS

| 7,022,075 B2 * | 4/2006 | Grunwald | ................ A61B 8/00 600/446 |
| 2002/0173721 A1 * | 11/2002 | Grunwald | ................ A61B 8/00 600/437 |

(Continued)

FOREIGN PATENT DOCUMENTS

| CN | 101002681 | 7/2007 |
| CN | 101317786 | 12/2008 |

(Continued)

OTHER PUBLICATIONS

"Office Action of China Counterpart Application," dated Aug. 2, 2018, pp. 1-10.

*Primary Examiner* — Michael Tomaszewski
(74) *Attorney, Agent, or Firm* — JCIPRNET

(57) ABSTRACT

The invention provides a medical image playing system for playing a continuous image corresponding to a particular region of the human body. The system includes: a main display module for displaying the continuous image, a sub display system for displaying at least one information of image sections of the continuous image, and an instruction receiving module for receiving at least an external instruction. The instruction receiving module is arranged in the sub display module and combined with the at least one information, such that when the instruction receiving module receives the at least one external instruction, the at least one information corresponding to the external instruction is transmitted to the main display module to display the image corresponding to the at least one information.

10 Claims, 4 Drawing Sheets

(56) References Cited

U.S. PATENT DOCUMENTS

2003/0013959 A1\* 1/2003 Grunwald ................ A61B 8/08
                                                         600/437
2003/0114743 A1   6/2003 Eck
2009/0082675 A1   3/2009 Gunji et al.

FOREIGN PATENT DOCUMENTS

| CN | 101779964  | 7/2010 |
| CN | 102440805  | 5/2012 |
| CN | 103654963  | 3/2014 |
| WO | 2014099825 | 6/2014 |

\* cited by examiner

MEDICAL IMAGE PLAYING SYSTEM AND METHOD

CROSS-REFERENCE TO RELATED APPLICATION

This application claims the priority benefit of Taiwan application serial no. 104104365, filed on Feb. 10, 2015. The entirety of the above-mentioned patent application is hereby incorporated by reference herein and made a part of this specification.

BACKGROUND OF THE INVENTION

1. Field of the Invention

The invention relates to an image playing system, and particularly relates to a medical image playing system and method.

2. Description of Related Art

In currently operation of playing a medical image, particularly an ultrasound scanning image of a region of the human body, the image is normally obtained through scanning the region and recording using an ultrasound scanning apparatus by the operator or physician. Then, the image is played by a special apparatus. However, the image is usually a long and continuous image. When the attention of the physician is distracted, even if the physician notices an abnormity in the image, the image may not be timely paused at the specific moment. Also, if the physician wishes to observe the abnormity again, the image must be played all over again. The aforementioned cases make the operation less convenient. Also, a position of the region of the human body corresponding to the abnormity must be recorded manually, which additionally consumes human resources to a certain extent. Moreover, while the accuracy of the image relies on how the operator or physician carries out a scanning process, whether there is any mistake committed during the scanning process cannot be known afterwards, which may result in decrease in medical quality.

Thus, how to develop a medical image playing system offering a more intuitive and convenient playback function and information as well as a function of examining whether a mistake is committed during the scanning process, so as to improve the medical quality, remains an issue to work on.

SUMMARY OF THE INVENTION

An embodiment of the invention provides a medical image playing system. The system plays a continuous image corresponding to a particular region of human body. The system includes a main display module, a sub display module, and an instruction receiving module. The main display module displays the continuous image. The sub display module displays at least one information of a plurality of image sections of the continuous image. The instruction receiving module receives at least one external instruction. In addition, the instruction receiving module is provided in the sub display module and combined with the at least one information such that when the instruction receiving module receives the at least one external instruction, the at least one information corresponding to the external instruction is transmitted to the main display module, so as to display the image corresponding to the at least one information. By providing the medical image playing system, a more convenient and less error-prone medical image playing function is provided.

An embodiment of the invention provides a medical image playing method. The method executes a medical image playing system to display a continuous image corresponding to a particular region of the human body. The method includes: displaying the continuous image by using a main display module; displaying at least one information of a plurality of image sections in the continuous image by using a sub display module; receiving at least one external instruction by using an instruction receiving module, wherein the external instruction is combined with the at least one information; transmitting the at least one information to the main display module based on the external instruction; and displaying the image section of the image sections corresponding to the at least one information by using the main display module. By providing the medical image playing method, a more convenient and less error-prone medical image playing function is provided.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
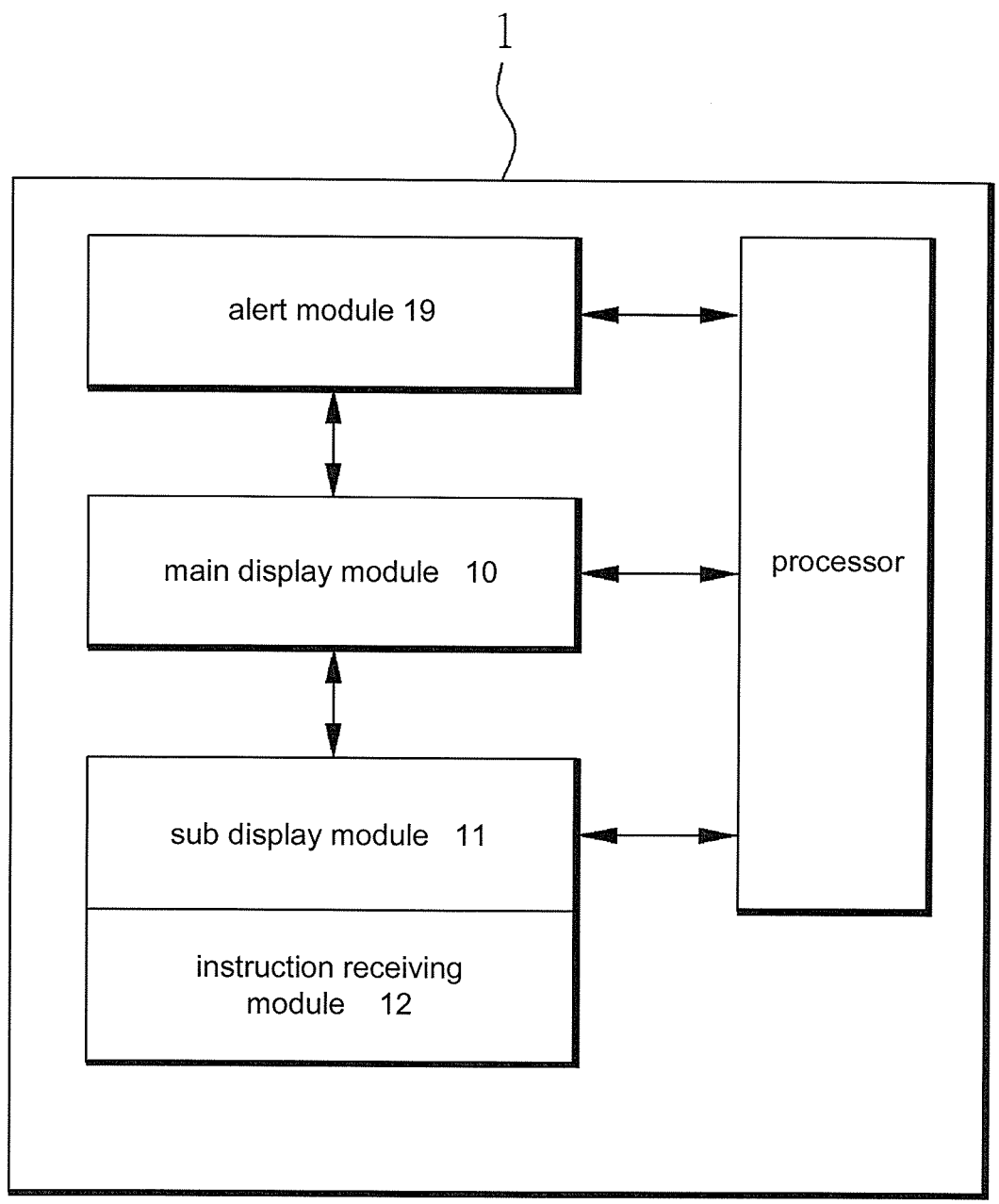
FIG. 1 is a schematic view illustrating a medical image playing system according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a schematic view illustrating a medical image playing system 1 according to an embodiment of the invention. The medical image playing system 1 mainly includes a main display module 10, a sub display module 11, an instruction receiving module 12, and an alert module 19. The medical image playing system 1 is configured to display a continuous image corresponding to a target range of a human body. The image is, for example, a handheld or automated ultrasonic scanning image of breast such as Automated Breast Ultrasound (ABUS) image. The medical image playing system 1 may read the continuous image and use the main display module 10 to play the continuous image. In addition, the medical image playing system 1 also uses the sub display module 11 to display information of a plurality of image sections of the continuous image, and uses the instruction receiving module 12 to receive at least one external instruction. Preferably, the main display module 10, the sub display module 11, the instruction receiving module 12, and the alert module 19 are connected with each other to respectively transmit signals, or are respectively connected to a processor such that the processor handles operations between the modules.

In particular, the instruction receiving module 12 is provided in the sub display module 11 and combined with the information of the image sections. Namely, when the instruction receiving module 12 receives the at least one external instruction, the instruction receiving module 12 may transmit, or transmit by using the processor, the information of at least one image section of the image sections corresponding to the external instruction to the main display module 10. The main display module 10 thus displays the image corresponding to the information.

Figure 2A:
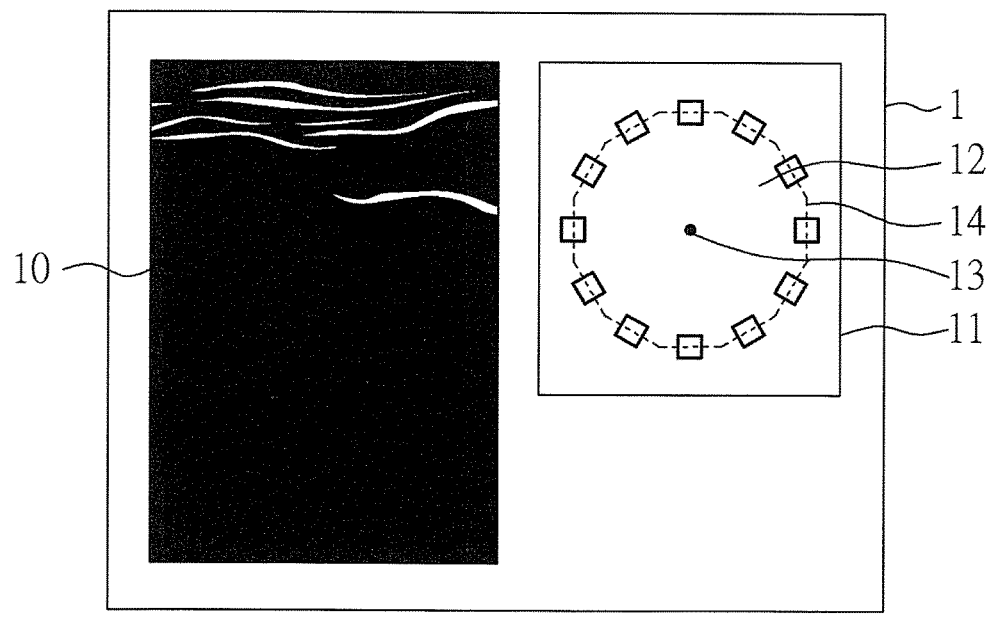
FIG. 2A is a schematic view illustrating a medical image playing system according to an exemplary embodiment of the invention.

FIG. 2A is a schematic view illustrating the medical image playing system 1 according to an exemplary embodiment of the invention. As shown in FIG. 2A, the main display module 10 is a playing area, whereas the sub display module 11 is another playing area. The main displaying module 10 displays an ultrasound image at a specific position of a particular region of the human body, and the information displayed by the sub display module 11 indicates information at the position of the region.

As shown in FIG. 2A, the sub display module 11 displays a reference point 13 and a range 14 centered on the reference point 13. The reference point 13 preferably corresponds to a starting point of the continuous image, such as a position where the particular region of the human body is firstly inspected. In other words, subsequent parts of the continuous image correspond to parts other than the position that is firstly detected. However, in other embodiments, the reference point 13 may not be the starting point of scanning, and may only serve as a reference point for positioning. Namely, a position corresponding to an arbitrary image section of the continuous image may serve as the reference point of other corresponding positions. The range 14 is preferably a range of a circle whose radius is a longest distance between a scanning position and the position that is firstly scanned of the particular region of the human body. However, the invention is not limited thereto. In practice, the range 14 may be a range in an arbitrary shape. However, to describe the invention in detail, a circular range is used in the following as an example to describe the embodiments.

Figures 2B, 2C:
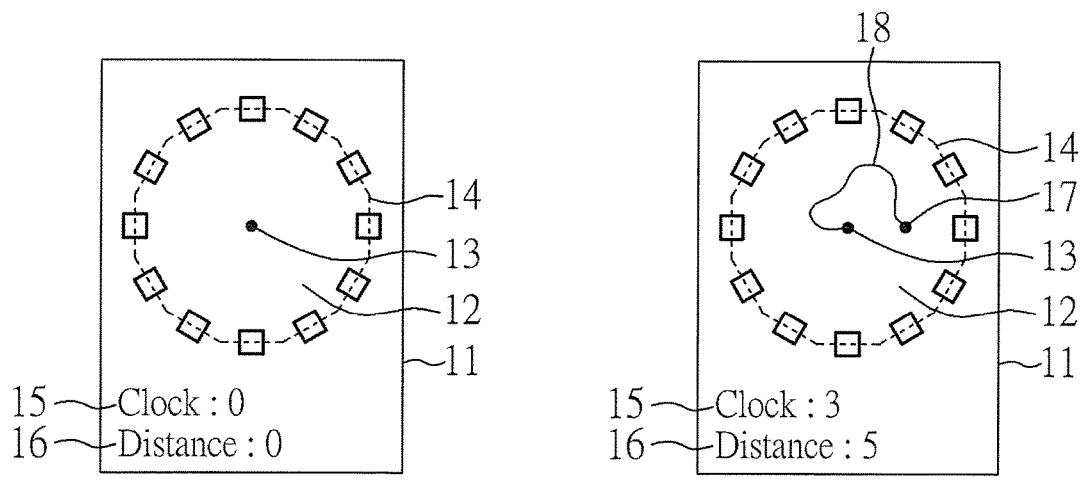
FIG. 2B is a schematic view illustrating a sub display module when the system starts to play an image.
FIG. 2C is a schematic view illustrating the sub display module when the system plays the image for a period of time.

FIG. 2B is a schematic view illustrating the sub display module 11 when the system 1 starts to play the image. The sub display module 11 may display direction information 15 and distance information 16. The direction information 15 indicates an o'clock direction that a currently displayed position is at with respect to the reference point 13, and the distance information indicates a distance between the currently displayed position and the reference point 13. In this embodiment, the reference point is set to be a corresponding scanning position at the starting point of the image. However, in practice, the reference point may be a scanning position corresponding to an arbitrary time period in the image. In other words, the reference point is not necessarily limited as corresponding to the starting point of the image. Here, since the figure illustrates a state where the system starts to play the continuous image, the direction information 15 and the distance information 16 are both 0.

FIG. 2C is a schematic view illustrating the sub display module 11 when the system 1 plays the image for a period of time. Here, the direction information is 3, indicating that a current scanning position 17 is at three o'clock direction with respect to the reference point 13, and the distance information 16 is 5, indicating that the distance between the scanning position and the reference point 13 is 5. Here, the distance may be set in various units, such as centimeter or millimeter, etc. Also, the sub display module 11 may further display a trace 18 along which the particular region of the human body is scanned, so as to make the information displayed clearer and completely display the scanning process. Accordingly, the sub display module 11 may display location information where the particular region of the human body is scanned.

In addition, since the instruction receiving module 12 is combined with the information displayed by the sub display module 11, the user may select any position in the circular range 14. At this time, the instruction receiving module 12 may receive a selection instruction from the user, and thus transmit, or transmit by using the processor, the direction information 15 and the distance information 16 of the selected position to the main display module 10, such that the main display module 10 displays the image when the position is scanned in the continuous image based on the direction information 15 and the distance information 16.

Figure 3:
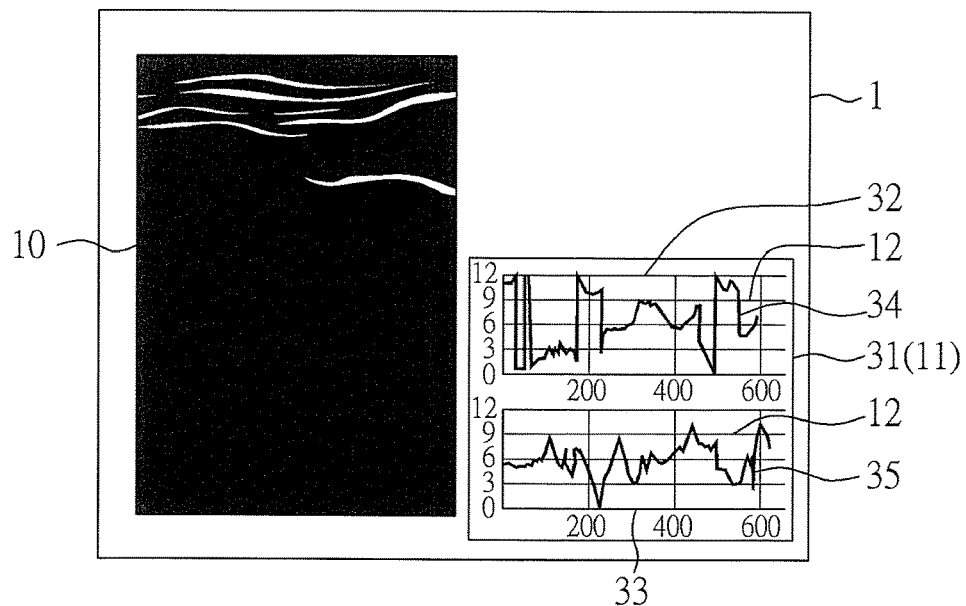
FIG. 3 is a schematic view illustrating a medical image playing system according to another exemplary embodiment of the invention.

FIG. 3 is a schematic view illustrating the medical image playing system 1 according to another exemplary embodiment of the invention. Similar to the embodiment shown in FIGS. 2A-2C, the main display module 10 of this embodiment also displays the ultrasound image at a position of the particular region of the human body, and information displayed in the sub display module 11 indicates information at the position of the region. However, as shown in FIG. 3, the sub display module 11 displays a table 31 illustrating a relation between a scanning position and time. Preferably, the table 31 may include two line charts, namely a line chart 32 showing the direction information in correspondence with time and a line chart 33 showing the distance information in correspondence with time.

The line chart 32 showing the direction information in correspondence with time (X-axis), and Y-axis thereof indicates 0 to 12, which represents an o'clock direction indicating the current scanning position of the particular region of the human body with respect to the reference point 13. The line chart 33 showing the distance information in correspondence with time (X-axis), and Y-axis thereof indicates 0 to an arbitrary value, which represents a distance between the current scanning position of the particular region of the human body and the reference point 13.

In this embodiment, the instruction receiving module 12 may still be combined with the information displayed in the sub display module 11. Therefore, the user may select an arbitrary position in the line chart 32 showing the direction information in correspondence with time or the line chart 33 showing the distance information in correspondence with time. At this time, the instruction receiving module 12 may receive a selection instruction from the user, and thus transmit, or transmit by using the processor, the direction information or the distance information of the position selected in the selection instruction to the main display module 10, such that the main display module 10 displays the image when the position is scanned in the continuous image based on the direction information 15 or the distance information 16. What differs from the previous embodiment is that the direction information or the distance information may be separately selected in this embodiment. When the direction information is selected, the main display module 10 may play all the images that match the direction information across the distance information (i.e., same direction, different distances). Alternatively, when the distance information is selected, the main display module 10 plays all the images that match the distance information (i.e., same direction but different directions).

In addition, lines 34 and 35 in the line charts may be set to display comprehensive location information when the continuous image starts being played. Namely, the moving trace (or scanning trace) of the region is numeralized to form the line 34 showing the direction corresponding to time and the line 35 showing the distance corresponding to time. In this way, the user may choose desired location information and make the main display module 10 directly play the scanning image of the location.

In yet another embodiment, the medical image playing system 1 may include the previous embodiments, such as being provided with a first sub display module to display the circular range (or substantially a range in an arbitrary shape) and a second sub display module to display the line charts at the same time.

Figure 4:
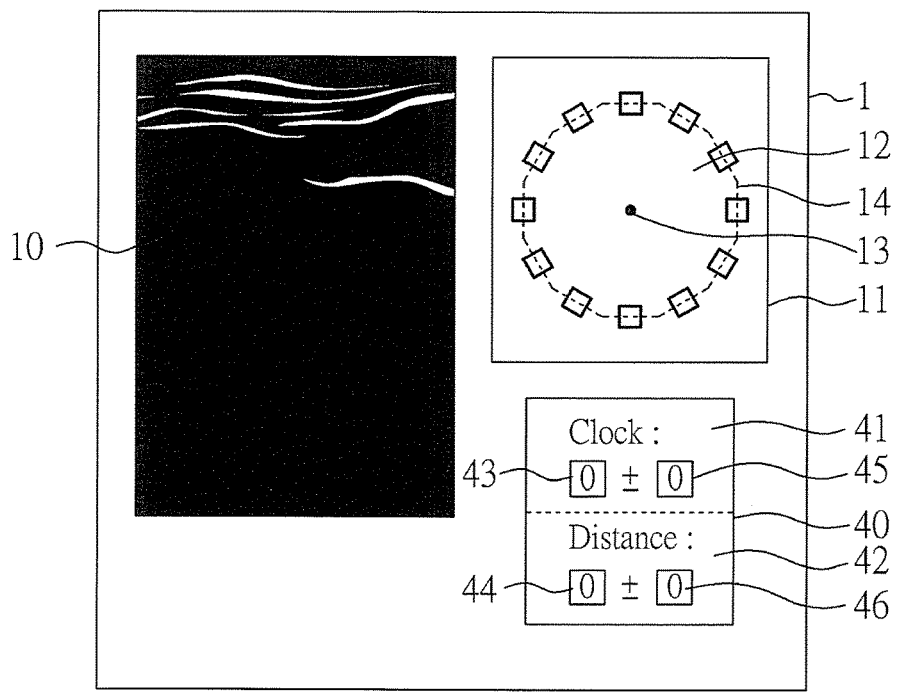
FIG. 4 is a schematic view illustrating an external instruction obtaining area of a medical image playing system according to an embodiment of the invention.

FIG. 4 is a schematic view illustrating an external instruction obtaining area according to an embodiment of the invention. As shown in FIG. 4, the medical image playing system 1 of the above embodiments may further include an external instruction obtaining module 40 including a direction obtaining area 41 and a distance obtaining area 42. The direction obtaining area 41 has a main direction obtaining area 43 for obtaining an instruction input by the user through the external instruction obtaining module 40. The instruction is an integer from 0 to 12, indicating the o'clock direction centered on the reference point 13. The distance obtaining area 42 also has a main distance obtaining area 44 for obtaining an instruction input by the user through the external instruction obtaining module 40. The instruction indicates the distance between the scanning position of the region of the human body and the reference point 13. In addition, the direction obtaining area 41 may have an auxiliary direction range area 45 for obtaining an auxiliary instruction to set a range for the direction. For example, if the external instruction obtained in the main direction obtaining area 43 is 5, and an instruction obtained from the auxiliary direction range area 45 is 1, it is indicated that a scanning position from four o'clock direction to six o'clock direction with respect to the reference point is requested. Similarly, the distance obtaining area 42 may further have an auxiliary distance range area 46 for setting a range for the requested distance.

Figure 5:
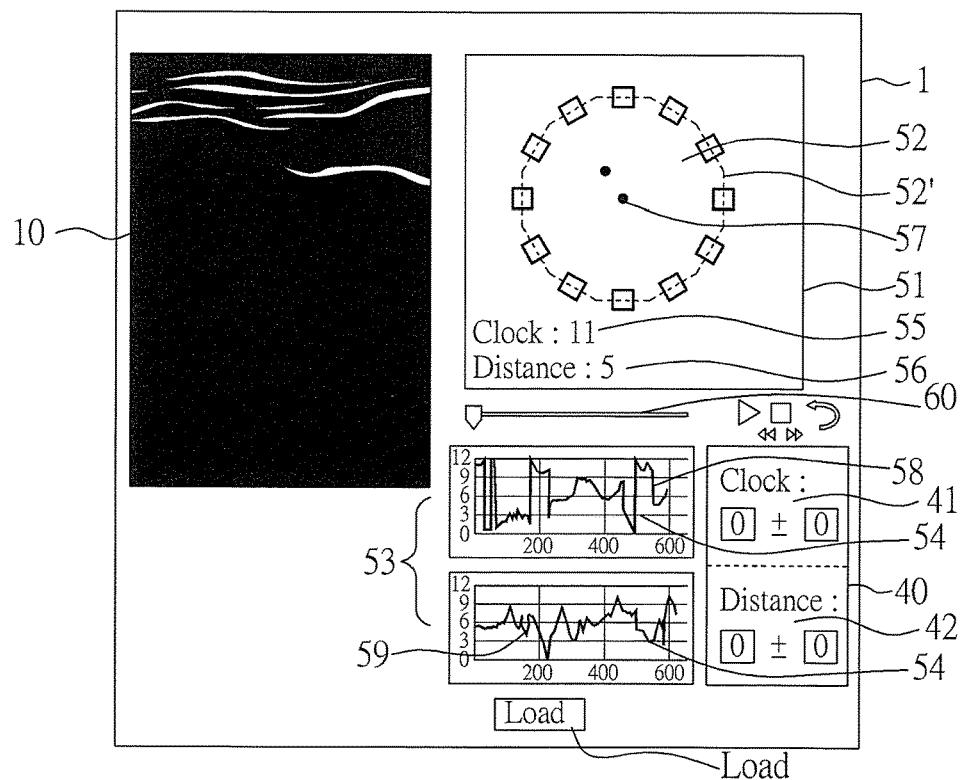
FIG. 5 is a schematic view illustrating an exemplary embodiment integrating several embodiments of the invention.

FIG. 5 is schematic view illustrating still another exemplary embodiment integrating the embodiments of the invention. The medical image playing system 1 of this embodiment has the main display module 10, a first sub display module 51, a first instruction receiving module 52, a second sub display module 53, a second instruction receiving module 54, and the external instruction obtaining module 40. The first sub display module 51 and the first instruction receiving module 52 are in the arrangement shown in FIGS. 2A to 2C. Namely, the first sub display module 51 displays a range 52' (a circular range is shown in the figure, but the range may be an arbitrary range) to display the scanning position of the particular region of the human body. The first sub display module 51 also provides direction information 55, distance information 56, and a reference point 57. The second sub display module 53 is similar to the display module 11 shown in the embodiment of FIG. 3, and the second instruction receiving module 54 is similar to the receiving module 12 shown in the embodiment of FIG. 3. Namely, two line charts 58 and 59 are displayed to indicate the scanning position of the region of the human body. The display module 10 and the external instruction obtaining module 40 are the same as those described in the embodiments. Moreover, the system 1 further includes a plurality of playing control keys to allow the user to perform functions such as playback, pause, rewind, forward, and replay, etc. Moreover, the system 1 may further include a plurality of special function keys, such that the user may perform functions such as reading a continuous image file, storing an image frame, etc.

Here, a process of executing the embodiments of the invention is described in detail with reference to the embodiment shown in FIG. 5. First of all, the user selects a read key "Load" in the medical image playing system 1, such that the medical image playing system 1 receives a read instruction and thus loads an ultrasound continuous image file of a particular region of the human body, such as an ultrasound continuous image file of breast. After the system 1 loads the image file, the main display module 10 displays a starting position of the continuous image (i.e., a position in 11 o'clock direction with respect to the reference point 57 and in a distance of 5 with respect to the reference point 57) and uses a reference point of the breast as the reference point 57. Here, the nipple is used as the reference point. However, the invention is not limited thereto. Any position may be set as the reference point. At this time, the direction information 55 on the first sub display module 51 is 11 and the distance information 56 on the first sub display module 51 is 5.

The user may choose the play key to make the system 1 start displaying the ultrasound continuous image of the breast on the main display module 10. As the time proceeds, a trace is generated in the range 52' displayed in the first sub display module 51 to display a process during which the position changes as the breast is scanned. In this embodiment, the range 52' is circular. However, the range may be in an arbitrary shape. At this time, the direction information 55 and the distance information 56 on the first sub display module 51 also change accordingly, and the main display module 10 displays the ultrasound image at a position of the trace. In addition, the line charts 58 and 59 of the second sub display module 53 also display the direction information and the distance information. Preferably, the current positions in the line charts 58 and 59 are indicated.

When viewing the continuous image displayed by the main display module 10, if the user finds an abnormality, the user may find out an abnormal position of the breast based on the range 52' and the line charts 58 and 59, and also find out whether a mistake is committed in the scanning process (e.g., whether the scanning speed is too fast (for example, to quantify the continuity of the moving trace by computing the distance between adjacent image sections) and whether the scanning is sufficiently complete (for example, to compute the coverage of moving trace in the range 52'), etc.). In this embodiment, the range 52' is circular. However, the range 52' may be in any arbitrary shape.

In response to the scanning speed being too fast that the distance between adjacent image sections larger than a distance threshold or the coverage of the moving trace in the range 52' being less than a coverage threshold, the alert module 19 may further make an alert for over speed or incompleteness of the scanning, to notify user of the medical image playing system. For example, the alert module 19 may display a notification (e.g. "the scanning speed is too fast" or "incompleteness") through the main display module 10 or make an alert sound through a speaker in response to an occurrence of the mistake. On the other hand, in response to the scanning speed being normal that the distance between adjacent image sections less than a distance threshold or the coverage of the moving trace in the range 52' being not less than the coverage threshold, the alert module 19 may also make a notification for normal speed or completeness of the scanning. It should be noticed that any type of notification or alert for the scanning speed or the scanning coverage would be applied in the embodiment, and the embodiment is not limited those notifications and alerts.

Moreover, the user may input a desired direction and a range value of the direction in the direction obtaining area 41 of the external instruction obtaining module 40 or input a desired distance and a range value of the distance in the distance obtaining area 42 to allow the main display module 10 to display the ultrasound image of the position. For example, if the user intends to view the ultrasound scanning image of the upper right side of the breast, the user may input 2 in the direction obtaining area 41 to indicate a position in two o'clock direction centered on the center of the breast and input the range value of 1 to indicate the image in 1 to 3 o'clock directions is requested to be displayed. Then, the user inputs a distance between the position that the user intends to view and the center point in the distance obtaining area 42. In addition, the user may directly select a desired position in the range 52' and the line charts 58 and 59, such that the main display module 10 displays the ultrasound image of the position. In this embodiment, the range 52' is circular, but the range may be in an arbitrary shape.

It should be noted that the image playing system 1 may further include a playing progress axis 60. The playing progress axis 60 indicates a playing progress of the continuous image and corresponds to the second sub display module 53. Namely, the information presented in the second sub display module 53 is the information of the scanning position in the playing progress.

Figure 6:
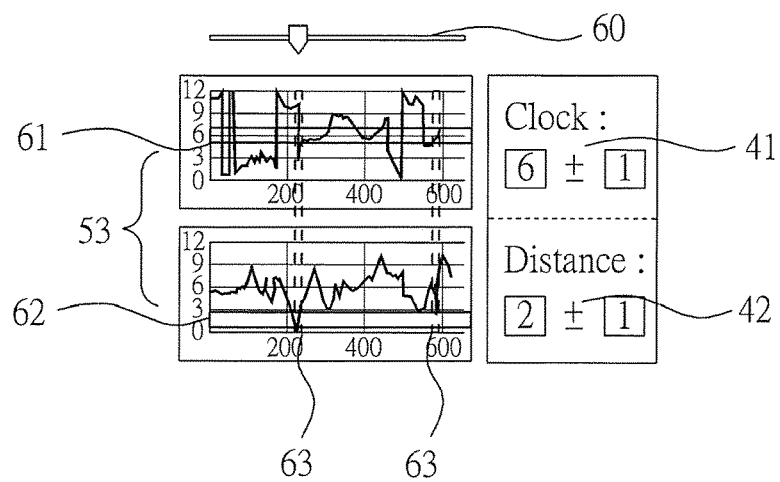
FIG. 6 is a schematic view illustrating a corresponding relation between a second sub display module and an external instruction obtaining area according to an embodiment of the invention.

In addition, the second sub display module 53 may be further integrated with the direction obtaining area 41 and the distance obtaining area 42. As shown in FIG. 6, when an external instruction relating to direction is obtained (e.g., the user inputs 6 o'clock direction and a range value of 1 in the direction obtaining area 41), the second sub display module 53 displays a direction condition range label 61 of the external instruction condition (i.e., 5 to 7 o'clock directions with respect to the reference point). Similarly, when an external instruction relating to distance is obtained (e.g., the user inputs a distance of 2 and a range value of 1 in the distance obtaining area 42), the second sub display module 53 displays a distance condition range label 62 of the condition (i.e., in a distance from 1 to 3 with respect to the reference point). In addition, when the conditions of direction and distance are both input, the direction obtaining area 41 and the distance obtaining area 42 may further display a direction-distance intersection label 63 to simultaneously display a range meeting the conditions of direction and distance. At this time, the user may find out the corresponding playing progress that meets the conditions on the second sub display module 53, and may directly select the progress on the playing progress axis 60 or record the progress to directly select the progress in later viewing. Furthermore, the first sub display module 51 may also be integrated with the direction obtaining area 41 and the distance obtaining area 42, so as to display a label (not shown) that meets the range conditions on the first sub display module 51.

It should be noticed that, the term "display module" (for example, the main display module 10, the sub display module 11, the first display module 51, and the second display module 54) in the embodiments of the present invention may be independent display modules or a combined module (e.g. the main display module 10 combines with the sub display module 11) such as Liquid Crystal Display (LCD), Organic Electro-Luminescent Display (OELD), etc. The term "instruction receiving module or instruction obtaining module" (for example, the instruction receiving module 12, the external instruction obtaining module 40, the first instruction receiving module 52, and the second instruction receiving module 54) in the embodiments of the present invention may be, for example, an input-output module such as a touch panel, a physical button, a switch, etc. The instruction receiving module or instruction obtaining module may display or provide at least one item corresponding to at least one instruction such as selection, parameter input, read instruction, etc for user input. Moreover, the term "processor" may be, for example, a central processing unit (CPU) or other programmable microprocessors for general purpose or special purpose, Digital Signal Processor (DSP), a programmable controller, Application Specific Integrated Circuit (ASIC) or other similar elements or a combination of above-mentioned elements. The alert module 19 may be a software program executed by the processor, or a physical controller or circuit for controlling the main display module 10 to display alert or notifications or a speaker to make a sound by transmitting control signal.

Accordingly, the embodiments of the invention provides the medical image playing system that provides a more convenient and less error-prone playing function, such that the physician may view the image section with an abnormality anytime. In addition, whether the scanning process carried out by the operator or physician is too fast or is sufficiently complete may be validated and alerted. Whether the scanning process is complete is determined by coverage that the moving trace covers the range 52', and whether the scanning speed is too fast is determined based on the continuity of the moving trace. Accordingly, the medical quality may be improved. Moreover, the medical image playing system is not only suitable for the handheld ultrasound scanning image but also suitable for the automatic ultrasound scanning image. Thus, the medical image playing system is highly adaptable.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A medical image playing system for displaying a continuous image corresponding to a particular region of a human body, the system comprising:
   a main display module, configured to display the continuous image;
   a sub display module, configured to display at least one information of a plurality of image sections in the continuous image; and
   an instruction receiving module, configured to receive at least one external instruction, wherein the instruction receiving module is disposed on the sub display module and combined with the at least one information, and in response to receiving the at least one external instruction, the instruction receiving module transmits the at least one information corresponding to the external instruction to the main display module, wherein the at least one information comprises a direction information and a distance information corresponding to a reference point of a particular region of the human body, wherein the main display module displays the image section corresponding to the direction information and the distance information corresponding to the reference point of the particular region of the human body in response to receiving the at least one information.

2. The medical image playing system as claimed in claim 1, further comprising a second sub display module and a second instruction receiving module, wherein the second sub display module is configured to display the at least one information of the image sections in the continuous image, and the second instruction receiving module is provided in the second sub display module and is combined with the at least one information.

3. The medical image playing system as claimed in claim 1, further comprising an external instruction obtaining area, configured to obtain an external input instruction of a range condition corresponding to a scanning position of the particular region of the human body, and the sub display module displays a label corresponding to the range condition.

4. The medical image playing system as claimed in claim 1, wherein the at least one information is a scanning position of the particular region of the human body corresponding to one of the image section.

5. The medical image playing system as claimed in claim 1, wherein the sub display module displays a moving trace corresponding to a scanning position of the particular region of the human body as playing of the continuous image proceeds, so as to determine a completeness of scanning based on a coverage that the moving trace covers the particular region of the human body, and determine whether a scanning speed is too fast based on a continuity of the moving trace; and the system further comprising:

an alert module, configured to make an alert for over speed or incompleteness of the scanning in response to the scanning speed being too fast that the distance between adjacent image sections larger than a distance threshold or the coverage of the moving trace in the particular region being less than a coverage threshold.

6. A medical image playing method for executing a medical image playing system to display a continuous image corresponding to a particular region of the human body, comprising:

displaying the continuous image by using a main display module;

displaying at least one information of a plurality of image sections in the continuous image by using a sub display module;

receiving at least one external instruction by using an instruction receiving module, wherein the external instruction is combined with the at least one information;

transmitting the at least one information to the main display module in response to receiving the external instruction, wherein the at least one information comprises a direction information and a distance information corresponding to a reference point of a particular region of the human body; and displaying the image section of the image sections corresponding to he direction information and the distance information corresponding to the reference point of the particular region of the human body in response to receiving the at least one information by using the main display module.

7. The medical image playing method as claimed in claim 6, further comprising displaying the at least one information of the image sections in the continuous image by using a second sub display module, wherein the second instruction receiving module is provided in the second sub display module and is combined with the at least one information.

8. The medical image playing method as claimed in claim 6, further comprising obtaining an external input instruction of a range condition corresponding to a scanning position of the particular region of the human body by using an external instruction obtaining area, and displaying a label corresponding to the range condition on the sub display module.

9. The medical image playing method as claimed in claim 6, wherein the at least one information is a scanning position of the particular region of the human body corresponding to one of the image section.

10. The medical image playing method as claimed in claim 6, wherein the sub display module displays a moving trace corresponding to a scanning position of the particular region of the human body as playing of the continuous image proceeds, so as to determine a completeness of scanning based on a coverage that the moving trace covers the particular region of the human body, determine whether a scanning speed is too fast based on a continuity of the moving trace, and make an alert for over speed or incompleteness of the scanning by using an alert module in response to the scanning speed being too fast that the distance between adjacent image sections larger than a distance threshold or the coverage of the moving trace in the particular region being less than a coverage threshold.

* * * * *